United States Patent [19]

Kinomoto et al.

[11] 4,386,336
[45] May 31, 1983

[54] HUMIDITY SENSOR AND A HUMIDITY DETECTION CIRCUIT USING THE HUMIDITY SENSOR

[75] Inventors: Shinichi Kinomoto, Kyoto; Masato Kawamura, Nishimachi; Susumu Kobayashi, Kanagawa, all of Japan

[73] Assignee: Shinyei Kaisha, Hyogo, Japan

[21] Appl. No.: 181,396

[22] Filed: Aug. 22, 1980

Related U.S. Application Data

[62] Division of Ser. No. 50,220, Jun. 20, 1979, Pat. No. 4,330,718.

[30] Foreign Application Priority Data

Aug. 24, 1978 [JP] Japan ................. 53-103474

[51] Int. Cl.$^3$ ............... H01L 7/00; B32B 15/08; G01N 25/64
[52] U.S. Cl. ...................... 338/35; 428/461; 428/463; 428/516; 428/520; 428/689; 526/292.2; 526/294; 526/295; 427/333; 427/341; 427/343; 307/118; 73/336.5
[58] Field of Search ............... 428/461, 516, 520, 689, 428/451, 463; 73/336.5; 526/292.2; 427/333, 341, 343; 338/35

[56] References Cited

U.S. PATENT DOCUMENTS

| | | | |
|---|---|---|---|
| 3,262,807 | 7/1966 | Sterman et al. | 428/520 X |
| 3,329,706 | 7/1967 | Sobolev | 526/292.2 |
| 3,559,456 | 2/1971 | Lomker et al. | 73/336.5 X |
| 3,671,913 | 6/1972 | Mamiya et al. | 73/336.5 |
| 3,802,268 | 4/1974 | Thoma | 73/336.5 |
| 3,914,982 | 10/1975 | Zanetti | 73/336.5 X |
| 4,035,500 | 7/1977 | Dafter, Jr. | 427/341 |

FOREIGN PATENT DOCUMENTS

55-81153   6/1980   Japan ................. 428/520

Primary Examiner—P Ives
Attorney, Agent, or Firm—Wenderoth, Lind & Ponack

[57] ABSTRACT

A humidity sensor as well as a humidity detection circuit are disclosed, the former employing a humidity sensitive material the electric resistance of which varies in response to the variance of humidity in an atmosphere and the latter employing such humidity sensitive material. The humidity sensor comprises a base plate made of alumina or the like with a humidity sensitive material formed on the base plate so as to form a film of a high molecular polymer unit which contains a reactive cationic monomer unit, is capable of detecting humidity over a wide range, shows little variance in nature in a high humidity atmosphere of organic gas, and has a long life. The humidity detection circuit comprises an oscillation circuit, a pair of electrodes which are connected by means of the humidity snesor and to one of which is supplied the output of the oscillation circuit as an input, and an amplifier circuit which is connected to the other one of the pair of electrodes. The humidity detection circuit is advantageous in that it can be used for a long period of time without varying the characteristics thereof.

11 Claims, 12 Drawing Figures

HUMIDITY SENSOR AND A HUMIDITY DETECTION CIRCUIT USING THE HUMIDITY SENSOR

This is a divisional application of application Ser. No. 50,220, filed June 20, 1979, now U.S. Pat. No. 4,330,718.

BACKGROUND OF THE INVENTION

The present invention relates to a humidity sensor, the electric resistance of which varies in response to the variance of humidity in an atmosphere.

Heretofore, various kinds of humidity sensors the electric resistance of which varies in response to the variance of humidity in an atmosphere have been known. However, they have drawbacks as mentioned below.

That is:

(1) a humidity sensor impregnated with an electrolyte salt such as lithium chloride etc.;

The humidity detection range of this humidity sensor is narrow. In addition, the life of this humidity sensor becomes extremely short in a high humidity atmosphere due to the fact that the electrolyte salt is diluted.

(2) a humidity sensor using a resin of humidity-absorbing nature into which an electrically conductive powder is mixed:

This humidity sensor is unable to detect a low humidity. In addition, this humidity sensor is inferior in its yield when it is produced as well as in its nature when it is used for a long period of time.

(3) a humidity sensor the surface of which is made of a metal oxide, e.g. aluminum oxide etc.:

This humidity sensor entails hysteresis and a reduction in sensitivity if the relative humidity becomes not less than 80%. In addition its nature deteriorates very rapidly in a high humidity atmosphere.

(4) a humidity sensor using a metal oxide:

The resistance of this humidity sensor is increased as time goes on and its nature varies in response to the changes in temperature. In addition, its manufacturing method becomes complex.

(5) a humidity sensor using a hydrophilic high molecular substance:

The "hydrophilic high molecular substance" means, for example, polyvinyl alcohol, polyvinyl acetate, polyvinyl pyrrolidone etc., which are soluble in water and the characteristic nature of which speedily deteriorates. This humidity sensor, which is used with its surface covered and mainly together with a semiconductor, is difficult to manufacture so as to have uniform characteristics. In addition, its characteristics are not stable and its life is short.

SUMMARY OF THE INVENTION

Accordingly it is an object of the present invention to provide a humidity sensor which has the following characteristics;

(1) To be able to detect humidity over a wide range from low humidity to high humidity.

(2) To show an increased variance in electric resistance with respect to the variance of humidity.

(3) To show little variance in characteristics even in an atmosphere containing organic gases.

(4) To show little variance in characteristics even in an atmosphere of high humidity.

(5) To show little hysteresis phenomena over all ranges of humidity.

(6) To be manufactured so as to have uniform characteristics.

(7) To be capable of using base plates of various kinds of nature and shape.

(8) To have a long life.

It is another object of the present invention to provide a humidity detection circuit which is capable of employing a humidity sensitive material of the above-mentioned characteristic nature for a long period of time without varying the characteristics.

It is another object of the present invention to provide a humidity sensor which is highly reliable and which has a long life by means of a humidity sensitive material of high molecular polymer material which contains a reactive cationic monomer unit.

It is another object of the present invention to provide a humidity detection circuit which comprises an oscillation circuit, a pair of electrodes which are connected by means of a high molecular polymer containing a reactive cationic monomer and to one of which is supplied the output of the oscillation circuit as an input, and an amplifier circuit which is connected to the other one of the pair of electrodes.

BRIEF DESCRIPTION OF THE DRAWINGS

Further objects and advantages of the present invention may be apparent from the following detailed description, taken with the accompanying drawings wherein.

DETAILED DESCRIPTION OF THE INVENTION

A humidity sensor according to the present invention will be explained in detail below.

Figure 1:
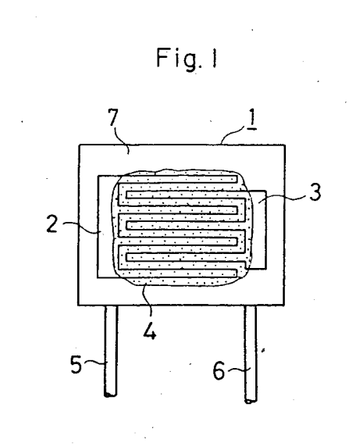
FIG. 1 is a front view of a humidity sensor according to the present invention.

The reference numeral 1 designates a humidity sensor of the present invention. The humidity sensor 1 comprises a base plate 7 made of alumina, a pair of comb-shaped electrodes 2, 3 which have gaps of predetermined dimensions and which are provided on the surface of base plate 7, a humidity sensitive material 4 which is provided on the surface of the electrodes and the surface of the base plate 7 so as to form a film, a lead 5 which is connected to the electrode 2 and a lead 6 which is connected to the electrode 3.

The humidity sensitive material 4 employed in the humidity sensor is a high molecular polymer containing a reactive cationic monomer unit. Such polymer units include the followings;

(1) a copolymer of a reactive cationic monomer unit and an organic monomer unit, (2) a copolymer of a reactive cationic monomer unit and an organic unit containing inorganic atoms, and (3) a homopolymer of a reactive cationic monomer unit.

The organic monomer unit which forms the first copolymer together with the reactive cationic monomer is a monomer unit with an ethylene unsaturated bond, a methacrylate or acrylate and the like. As the ethylene unsaturated compound, for example, the vinyl monomer $CH_2=CH-OH$, $CH_2=CH-CH_3$, $CH_2=CH-OCOCH_3$, $CH_2=CH-C_6H_5$ and $CH_2=CHCl$ may be employed.

As the acrylate or methacrylate, for example, diethyl hexyl methacrylate, isobutyl methacrylate, ethylene glycol dimethacrylate may be employed.

20-80 parts, preferably 50-70 parts, of the cationic monomer, 80-20 parts, preferably 50-30 parts, of the organic monomer and 0.5-4, preferably 1.5-2.5, parts of a polymerization initiator are copolymerized in a solvent, whereby a high molecular polymer containing a reactive cationic monomer unit is produced.

The organic unit containing inorganic atoms which forms the second copolymer together with the cationic monomer may be one with the elements of Si, B or P, for example, a silicon polymer, boron polymer, phosphoric acid polymer.

20-80 parts, preferably 50-70 parts, of reactive cationic monomer, 80-20 parts, preferably 50-30 parts, of the organic unit containing inorganic atoms and 0.5-4 parts, preferably 1.5-2.5 parts of a polymerization initiator are copolymerized in a solvent, whereby a high molecular polymer containing a cationic monomer unit is produced.

The homopolymer of a cationic monomer is produced by polymerizing 100 parts of reactive cationic monomer with the aid of 0.5-4 parts, preferably 1.5-2.5 parts, of a polymerization initiator in a solvent.

Some polymerizing methods will be concretely explained below.

If a mixture of 20-80 parts of 2-hydroxy-2-methacryloxypropyltrimethyl-ammonium chloride as the reactive cationic monomer, 80-20 parts of vinyl reactive cationic monomer, 80-20 parts of vinyl monomer as the organic monomer, 2 parts of benzoyl peroxide as the polymerization initiator and 5 parts of methanol as the solvent is heated at a temperature of 50°-120° C. for 5-15 hours, a solution of the copolymer unit of 2-hydroxy-3-methacryloxypropyltrimethyl-ammonium chloride and vinyl monomer is produced.

In this case, the kind and quantity of the polymerization initiator and the solvent may properly be changed within the scope which permits the polymerization.

If a mixture of 20-80 parts of 2-hydroxy-3-methacryloxypropyltrimethyl-ammonium chloride as the reactive cationic monomer, 80-20 parts of ethylene and/or $CH_2=CH-X$ (X: OH, $CH_3$, $OCOCH_3$, $C_6H_5$, Cl etc.) as the organic monomer unit, 2 parts of benzoyl peroxide as the polymerization initiator and 50 parts of methanol as the solvent is heated at a temperature of 50°-120° C. for 5-150 hours, a solution of 2-hydroxy-3-methacryloxypropyltrimethyl-ammonium chloride and ethylene and/or $CH_2=CH-X$ is produced.

In this case, the kind and quantity of the polymerization initiator and the solvent may be properly changed within the scope which permits the polymerization.

If a mixture of 20-80 parts of 2-hydroxy-3-methacryloxypropyltrimethyl-ammonium chloride as the reactive cationic monomer, 80-20 parts of polypropylene glycol monomethacrylate as the organic monomer, 2 parts of benzoyl peroxide as the polymerization initiator and 50 parts of methanol as the solvent is heated at a temperature of 50°-120° C. for 5-15 hours, a solution of a copolymer unit of said 2-hydroxy-3-methacryloxypropyltrimethyl-ammonium chloride and polypropylene glycol monomethacrylate is produced.

In this case, the kind and quantity of the polymerization initiator and the solvent may properly be changed within the scope to be able to effect the polymerization.

If a mixture of 45 parts of 2-hydroxy-3-methacryloxypropyltrimethyl-ammonium chloride as the reactive cationic monomer, 55 parts of 2-ethylhexyl methacrylate and/or isobutyl methacrylate as the organic monomer, 2 parts of benzoyl peroxide as the polymerization initiator and 20 parts of methanol as the solvent is heated at a temperature of 50°-120° C. for 5-15 hours, a solution of a copolymer unit of 2-hydroxy-3-methacryloxypropyltrimethyl-ammonium chloride and 2-ethylhexyl methacrylate and/or isobutyl methacrylate is produced.

In this case, the kind and quantity of the polymerization initiator and the solvent may properly be changed within the scope which permits the polymerization.

If a mixture of 100 parts of 2-hydroxy-3-methacryloxypropyltrimethyl-ammonium chloride as the cationic monomer, 2 parts of benzoyl peroxide as the polymerization initiator and 50 parts of methanol as the solvent is heated at a temperature of 50°-120° C. for 5-15 hours, a solution of a homopolymer of 2-hydroxy-3-methacryloxypropyltrimethyl-ammonium chloride is produced.

In this case, the kind and quantity of the polymerization initiator and the solvent may properly be changed within the scope which is sufficient to effect the polymerization.

Instead of using 2-hydroxy-3-methacryloxypropyltrimethyl-ammonium chloride as the reactive cationic monomer, methacrylethyltrimethyl-ammonium chloride can be employed.

Next, a method for fixing some humidity sensitive materials 4 which are produced as the solutions disclosed above on the surface of the base plate 7 between the electrodes 2, 3 shown in FIG. 1 will be explained.

That is, onto the surface of the electrodes 2, 3 and the surface of the base plate 7 between electrodes 2, 3 is adhered a solution of humidity sensitive material 4 by means of spraying, brushing, dipping or the like so as to form a film.

Immediately after this, drying and heating at a temperature of 100°-180° C. is effected, whereby said humidity sensitive material 4 is fixed onto the surface of the base plate 7 between the electrodes 2, 3 so as to connect the electrodes 2, 3.

Figure 2:
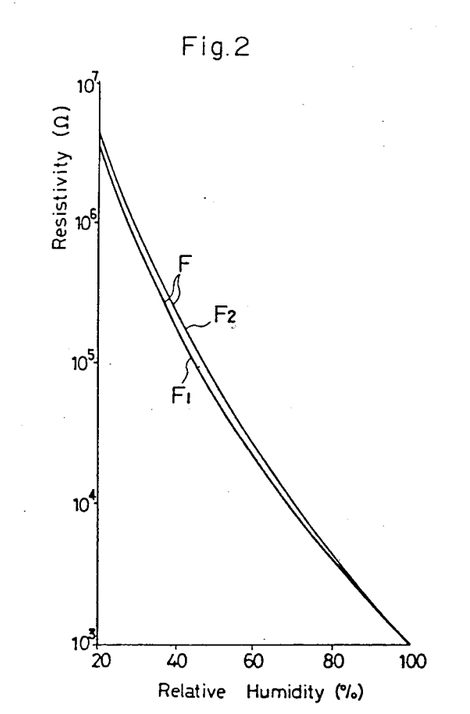
FIG. 2 is a graph showing characteristic curves of relative humidity vs. electrical resistance between electrodes in respect of humidity increasing and decreasing cases.

In FIG. 2, there are shown variances F in electrical resistance between the electrodes 2, 3 vs. variances in relative humidity of the humidity characteristic nature of the humidity sensor 1 in which the humidity sensitive material 4 as produced by the above-mentioned method is used.

$F_1$ in FIG. 2 shows a variance in resistance of the humidity sensor 1 when the relative humidity is increased from 20% to 100% and $F_2$ shows a variance in resistance of the humidity sensor 1 when the relative humidity is decreased from 100% to 20%. In this case, the difference between $F_1$ and $F_2$, that is, the hysteresis is approximately 1-2% of $F_1$, which is extremely small.

As clearly seen from FIG. 2, the electrical resistance of F is not more than $10^7 \Omega$ in the vicinity where the relative humidity is 20-30%, and the slope is extremely steep and furthermore the linearity between the logarithmic value of resistance and the relative humidity is excellent.

Figure 3:
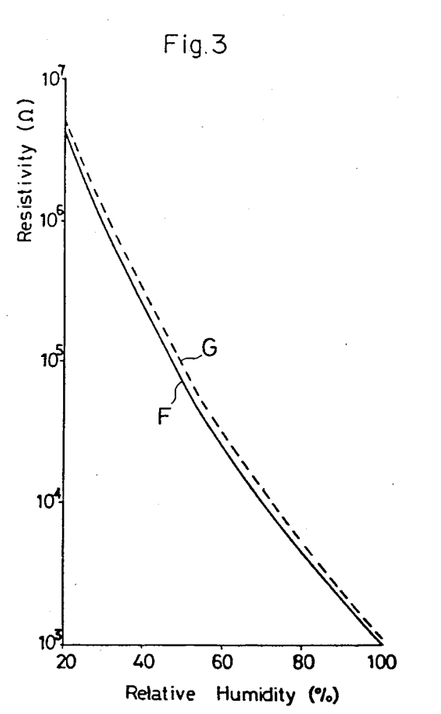
FIG. 3 is a graph showing a characteristic curve of relative humidity vs. electrical resistance between electrodes at a lapse of 500 hours after the cycle test in which a humidity sensor of the present invention is left in a relative humidity of 50% for 30 minutes and in a relative humidity of 90% for 30 minutes, together with an initial characteristic curve.

Next, FIG. 3 likewise shows test data with respect to the reliability and life of the humidity sensor of the present invention. The humidity characteristic nature indicated by F and G in FIG. 3 is such that F is the characteristic nature of the relative humidity vs. resistance measured prior to the test which is mentioned below, and G in FIG. 3 is the characteristic nature at a lapse of time of 500 hours after a cycle test, with one cycle to be left in a relative humidity of 50% for 30 minutes and thereafter be left in a relative humidity of 90% for 30 minutes. The smaller is the difference between the characteristic nature G and the characteristic nature F is, the better is the characteristic nature of reliability and life. In FIG. 3, the difference is approximately 1-2% of F and thus quite small, from which the humidity sensor of the present invention is considered to be excellent.

Next, an explanation will be made of a method of treatment to increase the life and improve the appearance by which the humidity sensor of the present invention is characterized.

That is, a solution of dichromic acid such as an ammonium dichromate is adhered so as to form a film on the surface of the humidity sensitive material 4 which is fixed on base plate 7 and thereafter a heat treatment is performed. Furthermore, a treatment with ultraviolet, electronic or other radiation is performed. Or, a treatment to acetalize the dichromic acid is performed after the treatment to adhere or cover with the solution of dichromic acid or salt to form the film. For example, a method to effect intermolecular cross-linking is given in which 50-30 parts by weight of acetic anhydride is reacted at a temperature of 50°-70° C. for 0.2-5 hours with 70-95 parts by weight of a reactive cationic monomer in a solvent.

The humidity sensor 1 for which the cross-linking treatment has been performed is characterized by the fact that its electric resistance increases uniformly approximately tenfold over the total range of the relative humidity and which becomes no drawback in use.

Next, an explanation is made based on the drawings of a humidity detection circuit in which the humidity sensitive material 4 as mentioned above according to the present invention can be used for a long period of time without varying its characteristic nature.

Figures 4, 5:
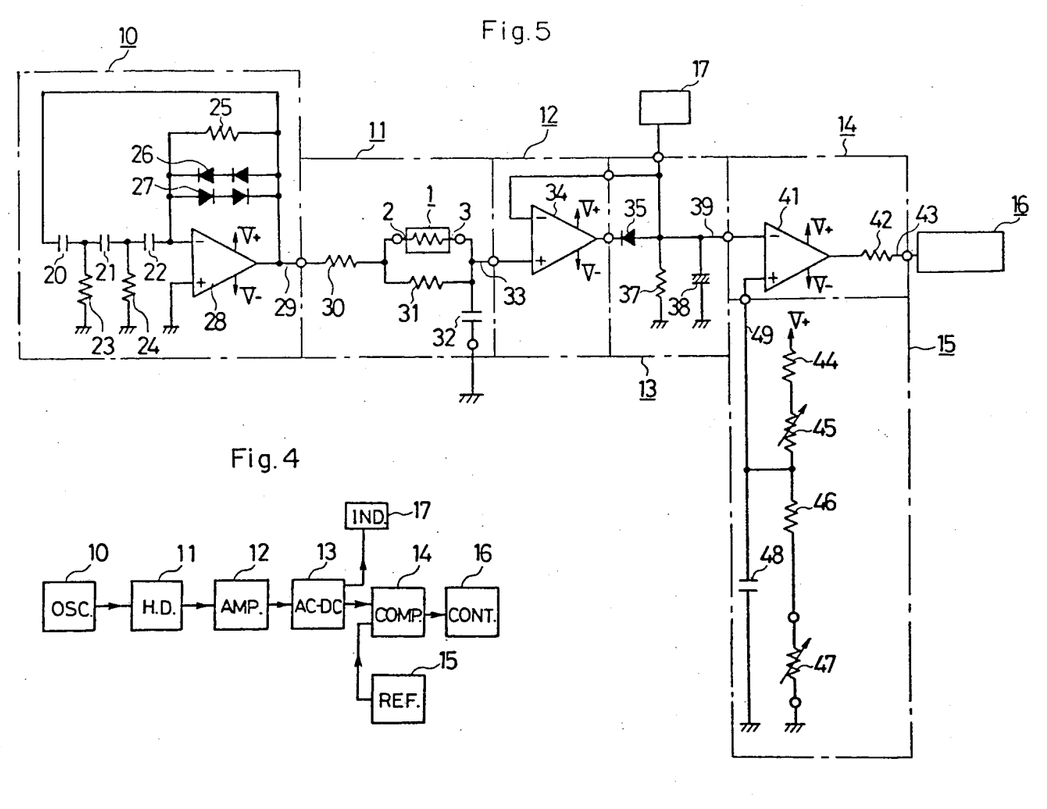
FIG. 4 is a block diagram of a humidity detection circuit in which a humidity sensor of the present invention can be used for a long period of time without varying its characteristic nature.
FIG. 5 is a circuit diagram by which the block diagram of FIG. 4 is rendered concrete.

In FIG. 4, which is a block diagram of the humidity detection circuit, there are provided an oscillation circuit 10 for generating an AC output, a humidity sensitive circuit 11 provided with a pair of electrodes 2, 3 which are connected by means of humidity sensitive material 4 and to one of which is supplied the output of the oscillation circuit 10 as an input, an amplifier circuit 12 which amplifies the other output of the pair of electrodes 2, 3, and AC-DC converter 13 which converts the AC output of the amplifier circuit 12 into a DC output, an indicator 17 which indicates the output of converter circuit 13, reference input circuit 15 which generates a reference input, a comparator circuit 14 which compares the output of AC-DC converter circuit 13 and the reference input of reference input circuit 15 and a control circuit 16 to which the output of comparator circuit 14 is supplied as an output and which controls an object to be controlled.

In FIG. 5, there is shown in detail the humidity detection circuit of the present invention which is shown as a block diagram in FIG. 4.

The oscillation circuit 10 includes an amplifier 28 the positive input terminal of which is earthed and the negative input terminal of which is connected to one end of a C-R block which consists of three condensors 20, 21, 22 connected in series and resistors 23, 24 respectively connected to two connections between adjacent condensors 20, 21, and 21, 22, respectively. The output terminal of amplifier 28 is connected to the other terminal of the C-R block and to an output terminal 29. The output terminal of the amplifier 28 is also connected to its negative input terminal via a parallel circuit of diodes 26, 27 which are respectively connected in the forward and backward directions and which control the amplitude of the oscillation output.

A resistor 25 which is connected in parallel with the parallel circuit of diodes 26, 27 controls the oscillation wave-form so as to become a sine wave or a rectangular wave in cooperation with the parallel circuit.

The humidity sensitive circuit 11 is provided with the humidity sensitive element 1 in which the humidity sensitive material 4 of the present invention is used and a resistor 31 is connected in parallel with element 1. One electrode 2 is connected to output terminal 29 of oscillation circuit 10 via resistor 30. The other electrode 3 of the humidity sensitive element 1 is connected to a condensor 32 which interrupts the DC component and to an output terminal 33.

The amplifier circuit 12 is provided with an amplifier 34 the positive input terminal of which is connected to the output terminal 33 of humidity sensitive circuit 11 and the output terminal of which is connected to the negative input terminal of the amplifier 34 via a diode 35 of the AC-DC converter circuit 13, which is discussed below.

The AC-DC converter circuit 13 is provided with the diode 35 which is connected between the output terminal of amplifier 34 and the negative input terminal thereof. The terminal of the diode 35 at the side of the negative input of amplifier 34 is connected to one end of a resistor 37 and a condensor 38 which are connected in parallel. The resistor 37 and the condensor 38 render smooth the AC output which is subjected to half-wave rectification and introduces the same to an output terminal 39.

The comparator circuit 14 is provided with an amplifier 41 the negative input terminal of which is connected to the output terminal 39 of converter circuit 13 and the positive input terminal of which is connected to an output terminal 49 of the reference input circuit 15, which is discussed below.

The amplifier 41 compares the output of AC-DC converter circuit 13 and the output of the reference input circuit 15, which is discussed below, and develops an output to a terminal 43 via a resistor 42.

The reference input circuit 15 is provided with a series circuit of a resistor 44 one end of which is connected to a DC power source, a half-fixed resistor 45 for correction, a resistor 46 and a variable resistor 47 for setting a reference value. The connection between the half-fixed resistor 45 and the resistor 46 of this series circuit is connected to a positive input terminal of the amplifier 41 of comparator circuit 14 via output terminal 49. To such connection of half-fixed resistor 45 and the resistor 46 is connected a condensor 48 for removing noise.

The control circuit 16 is connected to the output terminal of the comparator circuit 14 so as to control an object to be controlled (for example, an air-conditioner).

The function of the humidity detection circuit of the present invention which is constituted as mentioned above is as follows.

Figure 6:
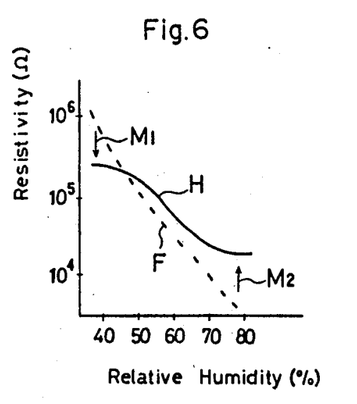
FIG. 6 is a graph explaining the function of the resistance of humidity sensitive circuitry.

That is, the amplifier 28 generates an AC voltage of a frequency which is determined by the C-R block consisting of the condensors 20, 21, 22 and the resistors 23, 24. This AC voltage is rendered so as to have a predetermined amplitude by means of the diodes 26, 27 and the resistor 25 and then is sent to one end of a circuit which consists of the resistors 30, 31 and the humidity sensitive element 1 via the terminal 29. This circuit which consists of the resistors 30, 31 and the humidity sensitive element 1 corrects the characteristic nature of relative humidity vs. electrical resistance between the electrodes 2, 3 of the humidity sensitive element 1 from F to H shown in FIG. 6. In other words, the resistance at low humidities is decreased (in the direction of $M_1$) by means of the resistor 31, and the resistance at high humidities is increased (in the direction of $M_2$) by means of the resistor 30.

Since the resistance of the circuit which consists of resistors 30, 31 and humidity sensitive element 1 varies in response to the relative humidity which is detected by means of the humidity sensitive element 1, the AC input from the output terminal 29 becomes an AC output which corresponds to the relative humidity detected and is supplied as an input to the positive input terminal of the amplifier 34 via the output terminal 33. The AC input from the output terminal 33 is amplified by the amplifier 34 and is subjected to half-wave rectification by means of the diode 35 and is further rendered smooth by means of the resistor 37 and the condensor 38 and is sent as an output of a DC voltage to the negative input terminal of the amplifier 41 via the output terminal 39.

On the other hand, the voltage at the connection between the half-fixed resistor 45 and the resistor 46 which is divided by means of the resistor 44, the half-fixed resistor 45, the resistor 46 and the variable resistor 47, is adjusted by means of the variable resistor 47 and is supplied as reference input to the positive input terminal of the amplifier 41 via the output terminal 49.

As a consequence, the amplifier 41 develops a voltage as a result of comparison of the value of the reference input, which is supplied as the input to the positive input terminal, and the output value, which corresponds to the relative humidity which is supplied as the input to the negative input terminal, to the control circuit 16 via the output terminal 43. The control circuit 16 controls the object to be controlled based on the input from output terminal 43.

Figure 7:
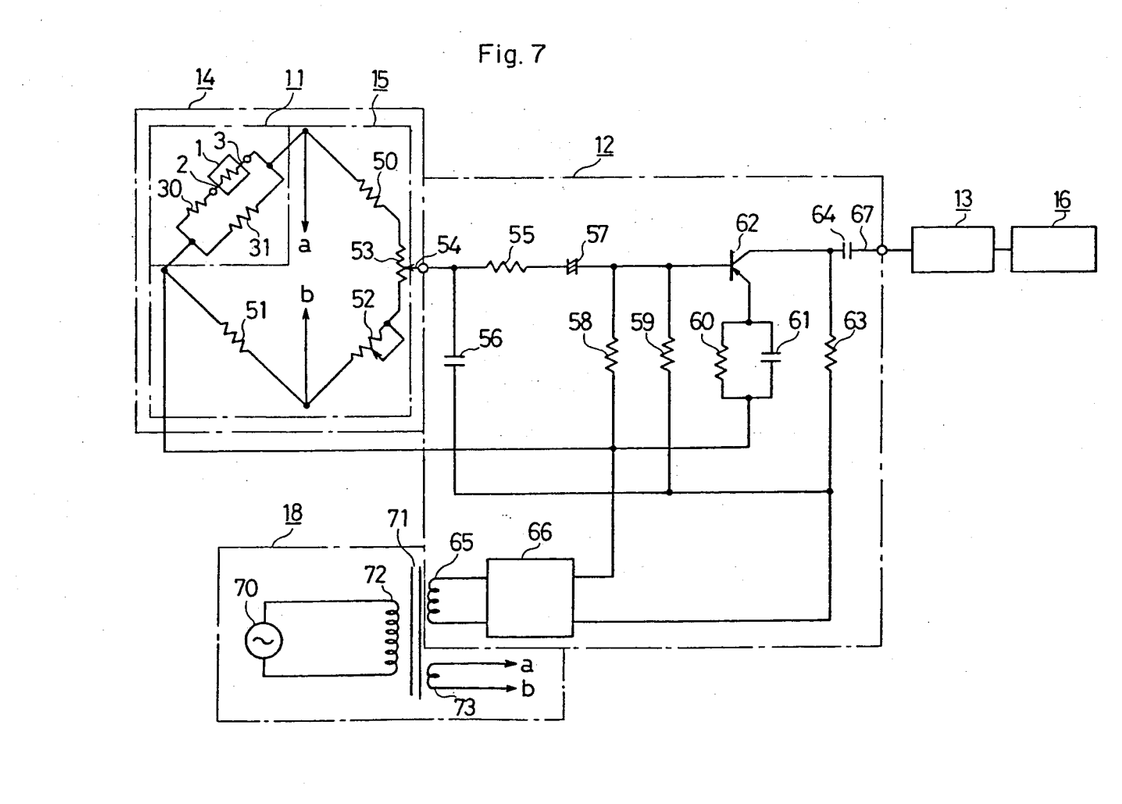
FIG. 7 is a circuit diagram of another humidity detection circuit in which a humidity sensitive material of the present invention can be used for a long period of time without varying its characteristics.

In FIG. 7, there is shown another humidity detection circuit of the present invention, which consists of blocks as explained below.

That is, the circuit is provided with a voltage transformer circuit 18 which transforms a voltage from an AC power source into a predetermined voltage, a humidity sensitive circuit 11 having the pair of electrodes 2, 3 which are connected by means of the humidity sensitive material 4 and to one of which is supplied the output of the voltage transformer 18, a reference input circuit 15 which generates a reference input, a comparator circuit 14 which compares the other output of the pair of electrodes 2, 3 and the reference input of the reference input circuit 15, an amplifier circuit 12 which amplifies the output of comparator circuit 14, a AC-DC converter circuit 13 which converts the AC output of amplifier circuit 12 into a DC, and a control circuit 16 to which the output of circuit 13 is supplied as an input and which controls the object to be controlled.

The details of each of the blocks are as follows.

That is, the voltage transformer circuit 18 is provided with an AC power source 70 which is connected to a primary winding 72 of a transformer 71 which generates a predetermined AC voltage across terminals (a) and (b) of the primary winding 72.

The humidity sensitive circuit 11 is provided with the humidity sensitive element 1 in which the humidity sensitive material 4 of the present invention is used. To one electrode 2 of element 1 is series connected resistor 30. In parallel with the series circuit of element 1 and resistor 30 is connected resistor 31.

The reference input circuit 15 is provided with a resistor 50, a resistor 51, a variable resistor 52 and a half-fixed resistor 53 which constitute a bridge circuit together with humidity sensitive circuit 11. The bridge circuit constitutes the comparator circuit 14 driven by means of the AC voltage which is supplied as an input from terminals (a) and (b) of voltage transformer circuit 18.

The amplifier circuit 12 has a transistor 62, the base of which is connected to a slider 54 of resistor 53 via a resistor 55 and a condensor 57 for interrupting the DC component, and the emitter of which is connected to the connection of the humidity sensitive circuit 11 to the bridge circuit which constitutes the comparator circuit 14 and the resistor 51 via a resistor 60 and a condensor 61.

On the other hand, the AC voltage which is supplied as an input to a secondary winding 65 of transformer 71 is converted into an AC voltage by means of a smoothing rectifier circuit 66, and a voltage which is determined by the resistors 58, 59 is biased across the base and the emitter of the transistor 62. Between the connection of humidity sensitive circuit 11 and resistor 51 and slider 54 is connected a condensor 56 for removing noise of a high frequency.

The collector of the transistor 62 is connected to a resistor 63 which converts the collector current into a voltage and develops an AC voltage as an output via a condensor 64 and an output terminal 67.

The AC-DC converter circuit 13 converts the input from the output terminal 67 into DC and sends an output DC voltage to the control circuit 16. The control circuit 16 controls the object to be controlled (for example, the air-conditioner) based on the input from the AC-DC converter circuit 13.

In comparison with the circuit shown in FIG. 4 and FIG. 5, the humidity detection circuit shown in FIG. 7 of the present invention which has the constitution and function as mentioned above is characterized by the following.

That is, in the circuits of FIG. 4 and FIG. 5, the input is supplied from the oscillation circuit 10, and the AC voltage which corresponds to the humidity by the humidity sensitive circuit 11 is once amplified determined by the amplifier circuit 12 and further is converted into DC by means of the AC-DC converter circuit 13 and then is compared with the reference input of the reference input circuit 15, whereby the object to be controlled is controlled.

On the contrary, in the circuit of FIG. 7, since the humidity sensitive circuit 11 and the reference input circuit 15 constitute the bridge circuit of the comparator circuit 14, what is amplified by means of the amplifier 12 is the differential component of the reference input and the AC voltage which is changed corresponding to the humidity detected by the humidity sensitive circuit 11.

In other words, the circuit in FIG. 7 employs the AC power source 70 whereby the oscillation circuit 10 in FIG. 4 and FIG. 5 is replaced by the voltage transformer circuit 18, and thus the circuit is rendered simple. What is more characteristic of the circuit is the simplification of the reference input circuit 15 by constituting the comparator circuit 14 as the bridge circuit.

The common characteristic of the humidity detection circuits of the present invention as shown in FIG. 4, FIG. 5 and FIG. 7 is that, despite the control operation being effected by means of switching, an AC voltage is applied to one of the electrodes of the humidity sensitive element 1 by means of the oscillation circuit 10 or voltage transformer circuit 18 and the humidity is extracted as an AC voltage output from another electrode 3 of the humidity sensitive element 1 for the following reasons.

That is, the electrical conductive mechanism of the humidity sensitive material of the present invention has the nature of ionic conduction resulting mainly from the cationic monomer.

Figure 8:
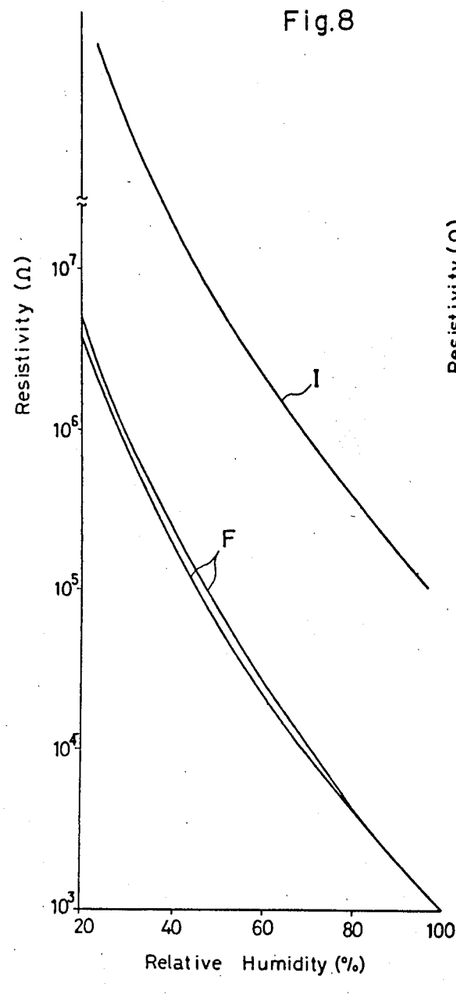
FIG. 8 is a graph explaining the reason why the humidity detection circuits of the present invention shown in FIG. 4, FIG. 5 and FIG. 7 apply an AC voltage to the humidity sensitive element by means of an oscillation circuit so that the humidity may be extracted as an output of an AC voltage.

As the result, a segregation is caused in the vicinity of the electrodes 2, 3 upon application of a DC voltage. In other words, if a DC voltage is applied to the humidity sensitive material 4 for a long period of time, the characteristic nature of the humidity sensitive material 4 deteriorates as indicated by I in FIG. 8 due to segregation, and thus the resistance is increased. Furthermore, if the DC voltage is kept applied for a long period of time, it may occur that the humidity sensitive material 4 will become broken. In order to prevent such occurrence, the AC voltage is applied to the humidity sensitive element 1.

Next will be explained a filter which is effective in case the humidity sensor of the present invention is used in the atmospheres mentioned below:

(1) an atmosphere containing ionizing substances;
(2) an atmosphere containing organic gases;
(3) an atmosphere containing tobacco smoke, dust, or the like;
(4) an atmosphere containing water drops.

Figure 9:
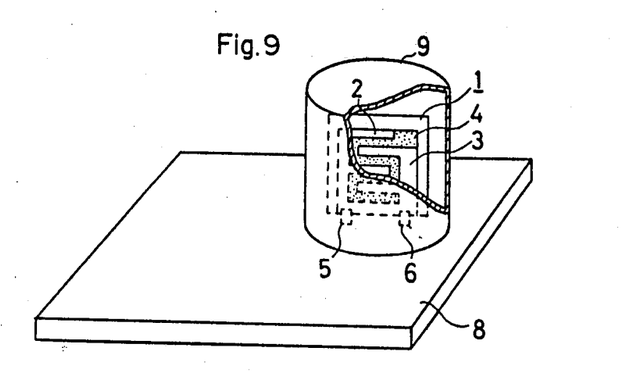
FIG. 9 is a perspective view of a filter for removing the solid and liquid components in an atmosphere.
Figure 10:
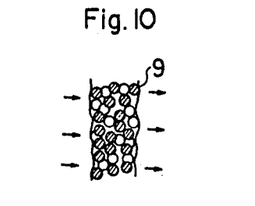
FIG. 10 is an enlarged cross-sectional view of the filter shown in FIG. 9.

FIG. 9 shows a filter 9 which is mounted on a mounting plate 8 so as to house the humidity sensitive element 1. The filter 9 is produced by pressing together a plurality of particles of acrylonitrile-styrene copolymer as shown in FIG. 10. That is, countless paths which wind from the front surface to the back surface are formed between the particles. As a consequence, filter 9 permits only the gaseous components in an atmosphere to pass and removes the solid and liquid components. Therefore, it becomes possible to protect the humidity sensitive element 1 from the harmful solid and liquid components in the atmosphere without impairing the humidity sensing function.

Figure 11:
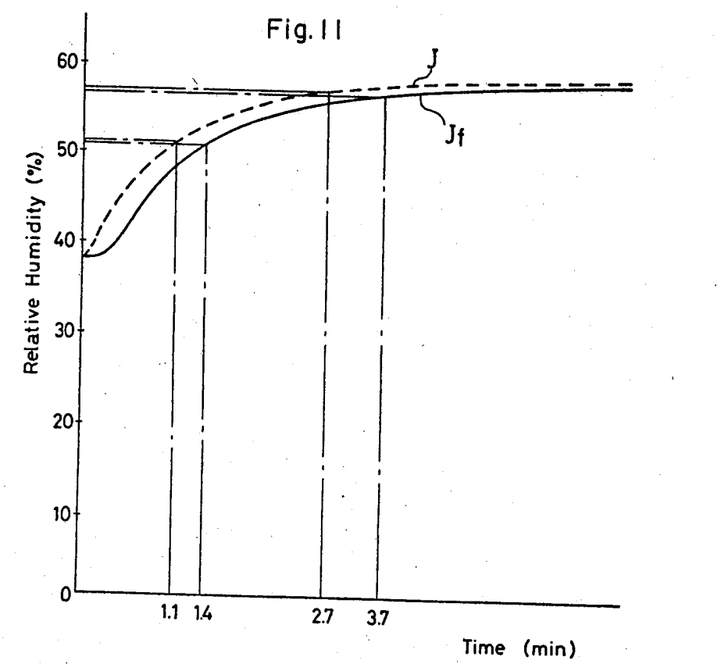
FIG. 11 is a comparative graph of the characteristic nature of a humidity sensor between the cases in which the filter shown in FIG. 9 is used and not used on an occasion when the relative humidity is varied from 40% to 60%.
Figure 12:
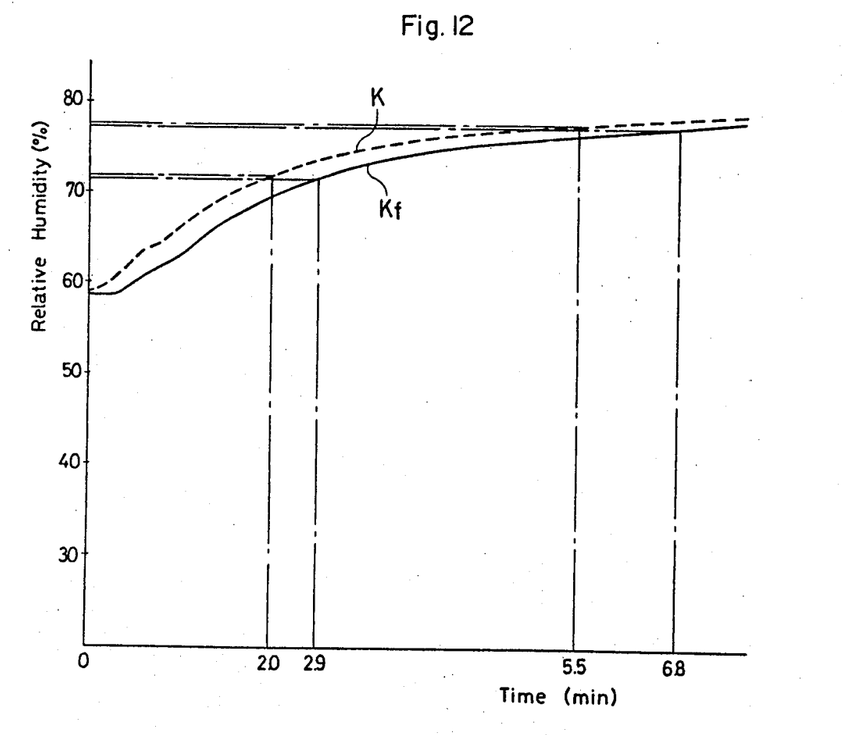
FIG. 12 is a comparative view of characteristic nature of a humidity sensor between the cases in which the filter shown in FIG. 9 is used and not used on an occasion when the relative humidity is varied from 60% to 80%.

In respect of the case where the filter 9 is produced by pressing together a plurality of particles of acrylonitrile-styrene copolymer so as to present a cylindrical shape as shown in FIG. 9 with an inner diameter of 10 mm, a height of 19 mm, a thickness of 3 mm, a porosity of 37.4% and a filtration of 100μ, FIG. 11 shows a humidity sensitive characteristic nature when the relative humidity is varied from 40% to 60% and FIG. 12 shows a humidity sensitive characteristic nature when a relative humidity is varied from 60% to 80%. The characteristic curve J in FIG. 11 and the characteristic curve K in FIG. 12 show the cases where the filter 9 is not used. The characteristic curve $J_f$ in FIG. 11 and the characteristic curve $K_f$ in FIG. 12 show the cases in which the filter 9 is used.

That is, it is seen that the humidity sensitive characteristic nature hardly deteriorates even if the filter 9 is used. Some hydrophobic substance of acrylonitrile-butadiene-styrene copolymer, polypropylene, polyethylene or the like may be used besides the acrylonitrile-styrene copolymer.

And if the filter 9 is made of a plurality of particles the diameters of which are uniform an advantage is brought about that the pressure loss becomes minor.

What is claimed is:

1. A humidity sensor comprising a base plate, a film on said base plate, and a pair of electrodes connected with said film, said film being a high molecular polymer having chloride ions in the polymer chain obtained by polymerizing a chloride ion-containing reactive cationic monomer alone or copolymerizing said cationic monomer with another monomeric component.

2. A humidity sensor as claimed in claim 1 which is housed in a filter made of a hydrophobic substance.

3. A humidity sensor as claimed in claim 1 wherein said polymer is a homopolymer of said reactive cationic monomer.

4. A humidity sensor as claimed in claim 3 wherein 2-hydroxy-3-methacryloxypropyltrimethyl-ammonium chloride or methacrylethyltrimethyl-ammonium chloride is employed as the reactive cationic monomer.

5. A humidity sensor as claimed in claim 1 wherein said film has been treated with dichromic acid or a salt thereof, followed by heating the thus treated film and then subjecting said film to radiation treatment or an acetalizing treatment.

6. A humidity sensor as claimed in claim 1 wherein said polymer is a copolymer of said reactive cationic monomer and an organic comonomer unit of at least one of an ethylenically unsaturated monomer, a methacrylate and an acrylate.

7. A humidity sensor as claimed in claim 6 wherein the copolymer is produced by copolymerizing 20-80 parts of reactive cationic monomer, 80-20 parts of organic comonomer and 0.5-4 parts of polymerization initiator in a solvent.

8. A humidity sensor as claimed in claim 6 wherein the copolymer is produced by copolymerizing 50-70 parts of reactive cationic monomer, 50-30 parts of organic comonomer and 0.5-4 parts of polymerization initiator in a solvent.

9. A humidity sensor as claimed in claim 1 wherein said polymer is a copolymer of said reactive cationic monomer and an organic unit containing Si, B or P.

10. A humidity sensor as claimed in claim 9 wherein the copolymer is produced by copolymerizing 20-80 parts of reactive cationic monomer, 80-20 parts of an organic unit containing Si, B or P, and 0.5-4 parts of polymerization initiator in a solvent.

11. A humidity sensor as claimed in claim 9 wherein the copolymer is produced by copolymerizing 50-70 parts of reactive cationic monomer, 50-30 parts of an organic unit containing Si, B or P, and 0.5-4 parts of polymerization initiator in a solvent.

* * * * *